United States Patent
Lad et al.

(10) Patent No.: US 10,918,517 B2
(45) Date of Patent: Feb. 16, 2021

(54) INTRAUTERINE DEVICE INSERTER

(71) Applicant: MERIL ENDO SURGERY PVT. LTD., Vapi (IN)

(72) Inventors: Nilay Mohanlal Lad, Vapi (IN); Chiragkumar Sumantrai Patel, Vapi (IN); Rajnikant Gandal Vyas, Mumbai (IN); Pramod Kumar Minocha, Vapi (IN)

(73) Assignee: MERIL ENDO SURGERY PVT. LTD., Vapi (IN)

( * ) Notice: Subject to any disclaimer, the term of this patent is extended or adjusted under 35 U.S.C. 154(b) by 614 days.

(21) Appl. No.: 15/688,854

(22) Filed: Aug. 28, 2017

(65) Prior Publication Data

US 2018/0055684 A1    Mar. 1, 2018

(51) Int. Cl.
*A61F 6/18* (2006.01)
*A61F 6/14* (2006.01)

(52) U.S. Cl.
CPC .............. *A61F 6/18* (2013.01); *A61F 6/144* (2013.01)

(58) Field of Classification Search
CPC ........ A61F 13/20; A61F 13/26; A61F 13/266; A61F 6/00; A61F 6/06; A61F 6/12; A61F 6/14; A61F 6/16; A61F 6/18; A61F 6/22; A61F 6/225; A61F 6/144; A61F 6/08; A61F 6/142; A61F 6/146; A61F 2006/045; A61F 2006/046; A61F 2006/048; A61F 13/2002; A61F 13/2011; A61F 13/34; A61F 2013/2014; A61F 13/263; A61F 13/28; A61F 2/0009; A61F 2/1662; A61F 2/1664; A61F 2/1667; A61F 2/167; A61F 2/1672; A61M 2205/02; A61M 2205/0238; A61M 2205/586; A61M 2210/14; A61M 2210/1433; A61M 31/007
USPC ................. 128/830, 831, 832, 833, 839, 840
See application file for complete search history.

(56) References Cited

U.S. PATENT DOCUMENTS

| | | | |
|---|---|---|---|
| 2013/0014762 A1* | 1/2013 | Deckman | A61F 6/144 128/833 |
| 2016/0217707 A1* | 7/2016 | Jutila | A61F 6/18 |
| 2017/0027739 A1* | 2/2017 | Deckman | A61F 6/18 |

* cited by examiner

*Primary Examiner* — Rachael E Bredefeld
*Assistant Examiner* — William T Kao
(74) *Attorney, Agent, or Firm* — Kunzler Bean & Adamson, PC (57) ABSTRACT

An inserter is provided which includes a handle having an upper cover and a bottom cover, the upper cover having a longitudinal opening, a proximal end and a distal end; a mounting member extending from an inner surface of the bottom cover of the handle, the mounting member having a through-hole; an inner tube having a proximal end and a distal end, the proximal end of the inner tube attached to the mounting member; an insertion tube movably coupled to the inner tube with a longitudinal axis essentially parallel to a longitudinal axis of the inner tube; a switch coupled to a proximal end of the insertion tube and arranged in the opening; and a string having a proximal end removably coupled near the proximal end of the opening, a distal end of the string coupled to a device to be inserted inside a human anatomy.

5 Claims, 8 Drawing Sheets

INTRAUTERINE DEVICE INSERTER

CROSS-REFERENCES TO RELATED APPLICATIONS

This patent application claims priority to Indian Patent Application Number 201621029221 entitled "INTRAUTERINE DEVICE INSERTER" and filed on Aug. 27, 2016 for Nilay Mohanlal Lad, et al., which is incorporated herein by reference in its entirety, for all purposes.

FIELD OF THE INVENTION

The invention relates to a medical device, specifically, the invention relates to an intrauterine device inserter.

BACKGROUND

Intrauterine device (IUD) placement is a medical procedure performed by medical professionals. The use of IUDs is an effective and popular form of contraception. It is an effective, easy to remove, satisfactory, and effortless method of reversible contraception for long term use. At present two types of IUDs are commonly available copper based IUDs and hormonal IUDs. The IUD is placed in the uterus through a cervix with an inserter. Most common inserters are constructed for introducing the device into the uterus in a contracted state. These inserters usually comprise an insertion tube and a plunger/inner tube inside the insertion tube. A string is attached to a proximal end of the IUD and extends through the full or partial length of the insertion tube. This string is provided in IUDs for two reasons. Firstly, it ensures the presence of the device in the body and secondly, the device is pulled out from the body by pulling the string. The string is released either by pushing the plunger/inner tube towards the uterus or by holding the plunger/inner tube steady and by retracting the insertion tube outwards. Once the device is out from the insertion tube within the uterine cavity, the device is supposed to resume its original expanded shape.

The inserters typically comprise some locking means for reversibly locking the intrauterine system in relation to the plunger/inner tube, said locking means being controllable by the slider and/or the insertion tube. Several mechanisms are currently available to lock one end of the string of the inserter device. For example, in some devices, the inserter end of the string is held by gears. Further, in some devices, the string is long due to which it is necessary to cut the string via for example, a sharp object. Although all these IUD insertion mechanisms work for their intended purpose, inserting these IUDs either requires additional time.

SUMMARY

In an embodiment of the present disclosure an inserter is provided. The inserter includes a handle having an upper cover and a bottom cover, the upper cover having a longitudinal opening, said opening having a longitudinal axis parallel to a longitudinal axis of the inserter, a proximal end and a distal end; a mounting member extending from an inner surface of the bottom cover of the handle, the mounting member having a through-hole; an inner tube having a proximal end and a distal end, the proximal end of the inner tube attached to the mounting member; an insertion tube movably coupled to the inner tube with a longitudinal axis essentially parallel to a longitudinal axis of the inner tube, the insertion tube having a proximal end and a distal end; a switch coupled to the proximal end of the insertion tube and arranged in the longitudinal opening; and a string having a proximal end and a distal end, the proximal end of the string removably coupled near the proximal end of the opening, the distal end of the string coupled to a device to be inserted inside a human anatomy.

In accordance with another embodiment, a method of operating an inserter is provided. The method includes the steps of introducing an insertion tube in a human anatomy up to a predefined depth; moving a switch from a distal position to a proximal positon, the movement of the switch exposes a device inside the human anatomy, the device is connected to a distal end of a string; removing a safety knob that holds a proximal end of the string; and withdrawing the insertion tube from the human anatomy leaving the device inside the human anatomy.

Other features of embodiments of the present disclosure will be apparent from accompanying drawings and from detailed description that follows.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific devices, methods and instrumentalities disclosed herein. Moreover, those in the art will understand that the drawings are not to scale. Wherever possible, like elements have been indicated by identical numbers.

DETAILED DESCRIPTION

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; Definitions of certain words and phrases are provided throughout this patent document, and those of ordinary skill in the art will understand that such definitions apply in many, if not most, instances to prior as well as future uses of such defined words and phrases.

Wherever possible, same reference numbers will be used throughout the drawings to refer to same or like parts. Moreover, references to various elements described herein are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Particular embodiments of the present disclosure are described herein below with reference to the accompanying drawings, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure provides an easy to use inserter which can be assembled easily for the insertion and to securely install and position an intrauterine system inside a human anatomy.

The inserter according to the invention is suitable for the positioning of intrauterine devices and intrauterine systems having different sizes and shapes. The inserter is especially suitable for installing intrauterine devices having a flexible frame having for example annular, circular, oval, spiral, toroidal, triangular, shield-like, almond-like, diamond-like, elliptical or polygonal shape. The inserter may further comprise means for holding and guiding the strings during the insertion so that no manual handling of said strings is needed.

In the present description and claims, the term proximal end refers to end of an element that is closer to a user of the inserter while the distal end refers to an end of the element which is farther from the user of the inserter. Moreover, the terms IUS or IUD and removal strings are used when describing the preferred embodiment of the present invention, but these are not to be construed as limiting the claims.

Figure 1A:
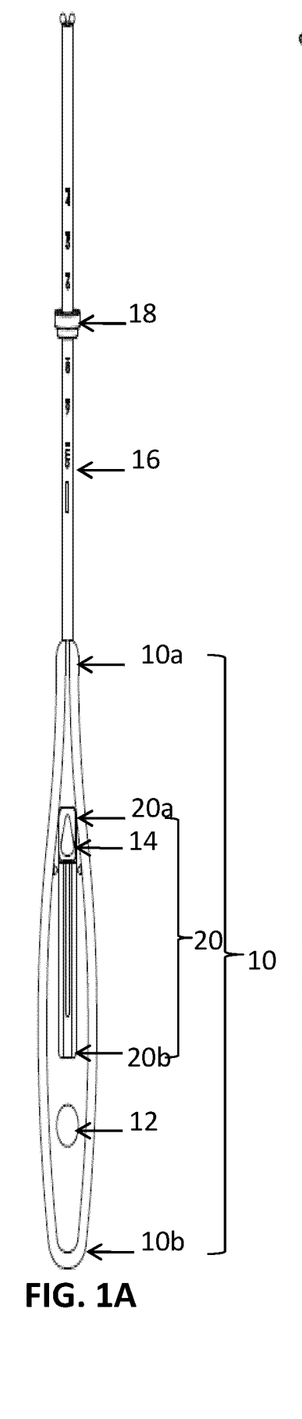
FIGS. 1A-1D depicts various exemplary two-dimensional representations of an intrauterine device (IUD) inserter 100.

FIG. 1A depicts a two-dimensional representation of an intrauterine device (IUD) inserter 100. The inserter includes a handle 10, a safety knob 12, a switch 14, an insertion tube 16, and a flange 18. The safety knob 12 and the switch 14 are provided with the handle 10 as explained below. The proximal end of the insertion tube 16 is enclosed inside the handle 10 while the flange 18 is mounted on the tube 16.

Figure 1B:
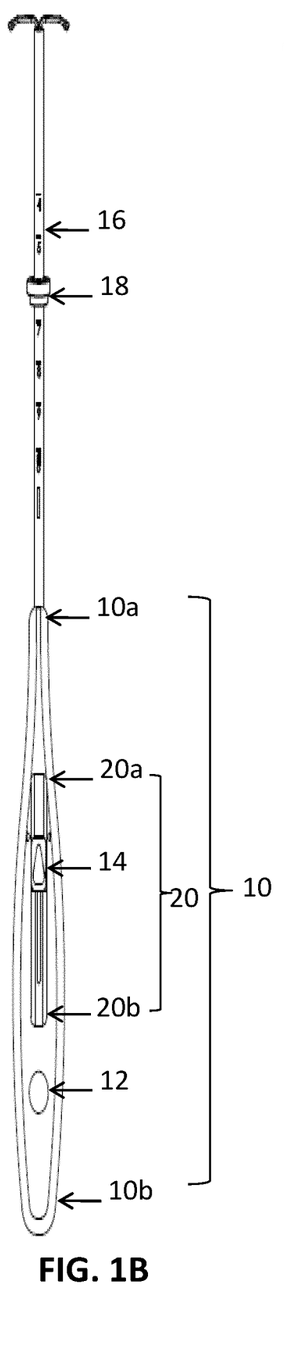
Figure 1C:
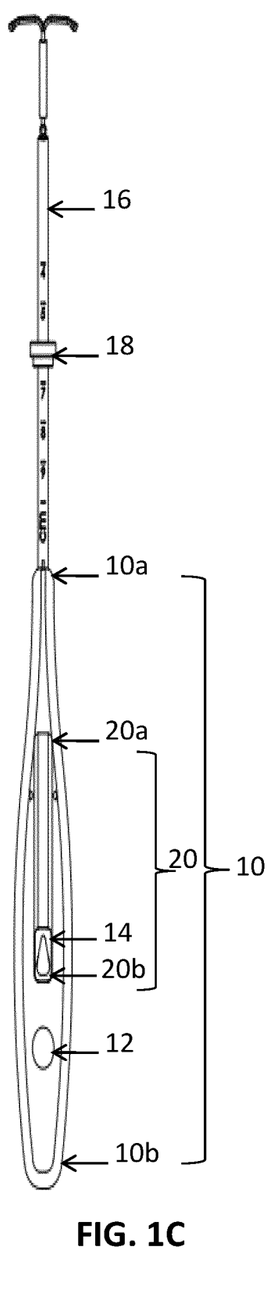
Figure 1D:
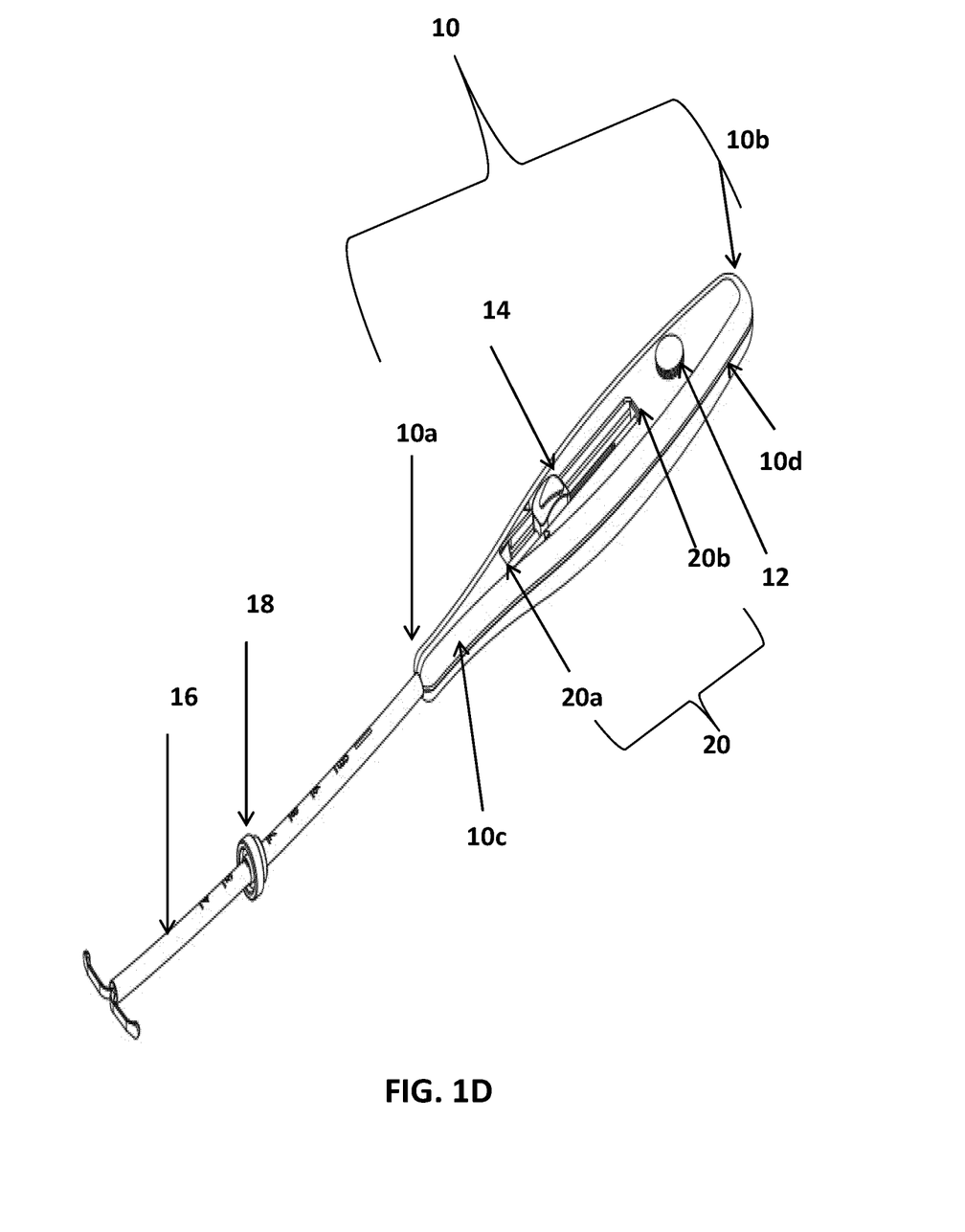

The handle 10 has a distal end 10a, a proximal end 10b, an upper cover 10c (FIG. 1D) and a bottom cover 10d (FIG. 1D). The handle 10 enables a surgeon or a user to grip and operate the inserter 100. The upper cover 10c (FIG. 1D) of the handle 10 includes a longitudinal opening 20. In the depicted embodiment, the opening 20 is shown to be positioned in the mid-portion of the upper cover 10c (FIG. 1D) of the handle 10 parallel to the longitudinal axis of the inserter. However, the opening 20 may be symmetrically or asymmetrically positioned on the handle. Further, the width of the opening 20 can be narrow or wide depending upon the size of the switch 14. The opening 20 has a distal end 20a and a proximal end 20b which act as the extreme positions to which the switch 14 can be positioned (further explained in FIGS. 1B and 1C). The handle also preferably has a hole (not shown) at its distal end 10a through which the insertion tube 16 passes and operatively couples with the opening 20 via switch 14. The handle 10 can have many shapes and is designed for easy handling of the inserter 100 even by using only one hand. The handle 10 can be made of without limitation of acrylonitrile butadiene styrene (ABS), polypropylene, high density polyethylene (HDPE), low density polyethylene (LDPE), polycarbonate, polyvinylchloride (PVC) etc.

The safety knob 12 has a top end and a stem (not shown) coupled to the top end. The stem (not shown) passes through a hole provided in the handle 10 further explained in FIGS. 2A-2E. The safety knob 12 holds the proximal end of a string in position.

The movable switch 14 is arranged in the opening 20. The switch 14 can be moved in the longitudinal direction of the insertion tube 16. Due to the movement of the switch 14, the insertion tube 16 is extended or retracted thereby closing or exposing a T-frame respectively. The switch can be made of plastic, polymer, etc. and can be of any shape including without limitation square, rectangular, triangular, etc. According to an embodiment of the present disclosure, the switch 14 comprises a means to move the slider, which preferably is a part of the switch 14. According to another embodiment of the present disclosure, the slider comprises at least two elements, preferably parallel, which are combined on at least one point by a transversal member. The transversal member may form means, for example a knob or switch, by which the slider can be moved. The handle can comprise one or more means to adapt the slider elements and to facilitate the movement of the switch, for example a support, a shoulder, a holder, a saddle, a groove or a slot.

The insertion tube 16 is a flexible and hollow tube whose proximal end is enclosed inside the handle 10 while the distal end houses the T-frame. The tube 16 is moveably coupled to the handle 10. In an embodiment, markings are provided on the tube 16 that help a user to place the inserter at an accurate location inside a human anatomy. The tube 16 can be straight or curved tube so as to conform to the human anatomy. The insertion tube is made of a relatively flexible material like polypropylene, low density polyethylene (LDPE), polycarbonate, polyvinylchloride (PVC) etc.

The flange 18 is arranged around the distal end of the insertion tube 16 for marking the depth up to which the inserter 100 is to be inserted inside a human anatomy. The flange 18 is a hollow circular structure that movable longitudinally over the insertion tube 16. To ensure the correct positioning of the intrauterine system in the uterus, the flange 18 is adjusted to correspond to the depth at which the inserter 100 will be inserted, said depth being beforehand determined by for example, using a sound or a probe.

In the FIG. 1A, the switch is positioned at the distal end 20a of the opening 20. In this position, the insertion tube 16 is fully extended such that it covers the T-frame provided in its lumen at the distal end 16a. The string (not shown) is held by the safety knob 12.

FIG. 1B depicts the intrauterine device (IUD) inserter 100 with the switch 14 positioned mid-way between the extreme ends of the opening 20 as denoted by the arrow 40. This may be referred as an initial position. In this position, the insertion tube 16 is not fully extended and the wings of the T-frame are exposed.

FIG. 1C depicts the intrauterine device (IUD) inserter 100 with the switch 14 positioned at the proximal end 10b of the handle 10. In this position, the insertion tube 16 is fully retracted due to which the T-frame is completely exposed. The T-frame is a device with two wings mounted on and extending away from a tube and contains a drug to be periodically released with the human anatomy where the T-frame is placed. The T-frame depicted on the figures is exemplary and can be replaced by any known T-frames that serve the desired purpose.

FIG. 1D depicts the three-dimensional assembly of the inserter 100. In this figure, the upper cover 10c and a bottom cover 10d of the handle 10 are clearly illustrated. Within the two covers, the internal assembly of various components is provided and explained with reference to the figures below.

FIGS. 2A-2E provides exemplary illustrations of the assembly of the handle 10 of the inserter 100.

Figure 2A:
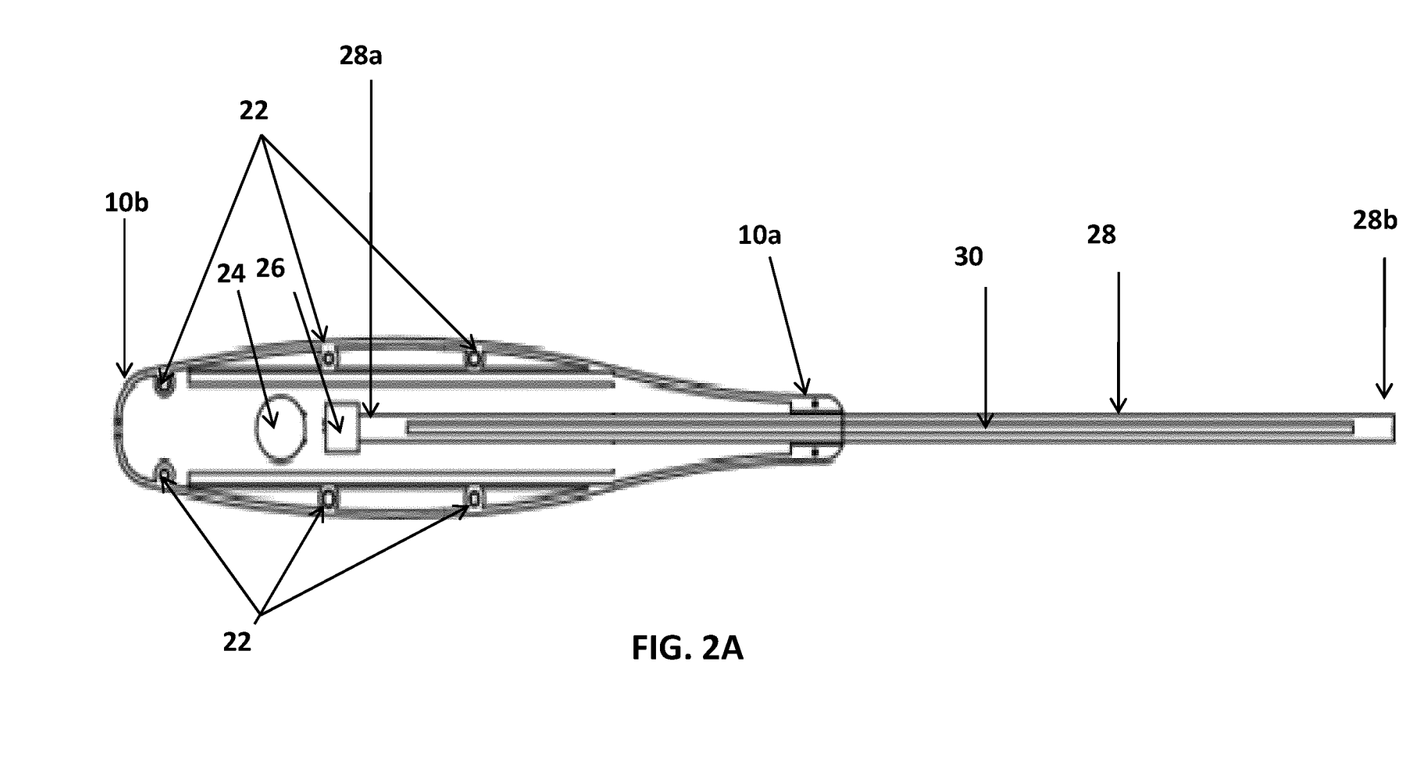
FIGS. 2A-2E provides exemplary illustrations of the assembly of the handle 10 of the inserter 100.

FIG. 2A depicts the inner portion of the bottom cover 10*d* of the inserter's handle 10. The inner portion includes multiple holes/protrusions 22, a knob hole 24, a mounting member 26, and an inner tube 28. The holes/protrusions 22 are provided at the inner periphery of the bottom cover 10*d*. The number of holes/protrusions 22 may vary. The holes/protrusions 22 mate with the corresponding protrusions/holes provided on the inner periphery of the upper cover 10*c* while assembling the handle 10.

The knob hole 24 is provided to mate with the stem of the safety knob 12. A string attached to the proximal end of a T-frame 32 (FIG. 2B) is wound around the knob hole 24 to hold the T-frame 32 (FIG. 2B) in position.

The mounting member 26 is provided in close vicinity of the knob hole 24. In an embodiment, the mounting member 26 contains a through-hole via which the proximal portion of the string of the T-frame 32 (FIG. 2B) passes before being wound around the knob hole 24. The mounting member 26 is made of a rigid material like acrylonitrile butadiene styrene (ABS), polypropylene, high density polyethylene (HDPE), low density polyethylene (LDPE), polycarbonate, polyvinylchloride (PVC), etc.

The inner tube 28 has a proximal end 28*a* and a distal end 28*b*. The proximal end 28*a* of the inner tube 28 is fixedly attached to the mounting member 26. Alternately, the inner tube 28 may be removably attached to the mounting member 26. The inner tube 28 is hollow and contains a lumen through which the string of the T-frame 32 (FIG. 2B) passes. The proximal end of the string passes through the proximal end 28*a* of the inner tube 28 and then the through-hole of the mounting member 26. In an embodiment, the inner tube 28 contains a slot 30 that extends through the majority of the length of the tube 28. The slot 30 allows the string to slide freely in it, without any risk of them getting jammed between the inner tube 28 and the insertion tube.

In an embodiment, to enable the optimal and secure positioning of the intrauterine system in the inserter 100, the distal end of the inner tube 28 is shaped to the form of a slot or an extension to adapt the reservoir of the intrauterine system. This ensures that the intrauterine system, namely, the T-frame does not drop or be twisted during insertion procedure and assumes a specified constant configuration when released.

Figure 2B:
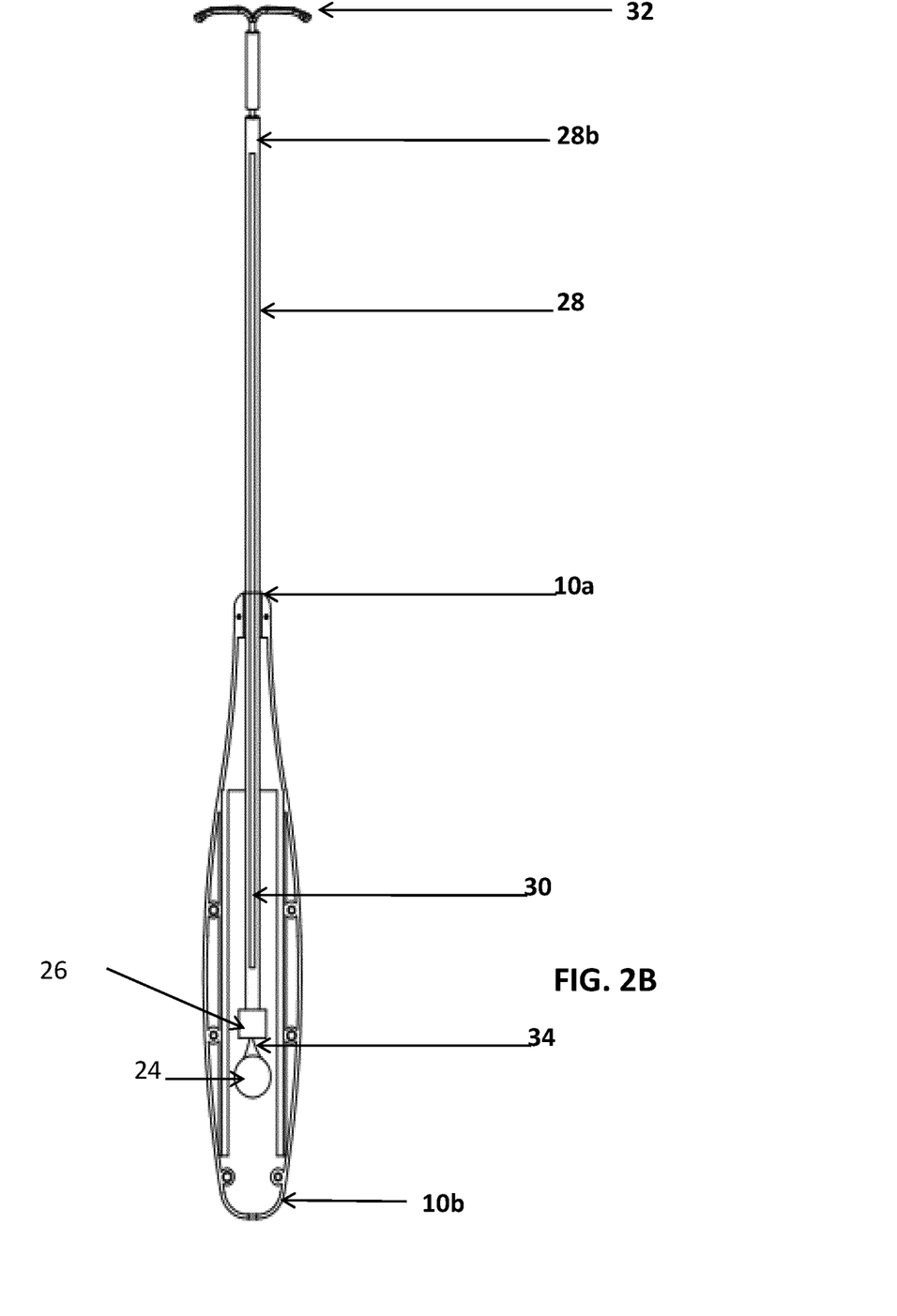

FIG. 2B illustrates the assembly of FIG. 2A with the T-frame 32. As stated above, the T-frame 32 is provided at the distal end 28*b* of the inner tube 28. The string of the T-frame 32 passes through a lumen of the inner tube 28, then the through-hole of the mounting member 26 and is finally wound around the knob hole 24. The string is closed at the proximal end via for example, a knot, gluing, bonding, etc. In an embodiment, the length of the string is so selected that it corresponds to the summation of the length of the inner tube 28, width of the mounting member 26 and the distance between the mounting member 26 and knob hole 24. This ensures that the T-frame 32 is held in position without the chances of the string being dislocated.

Figure 2C:
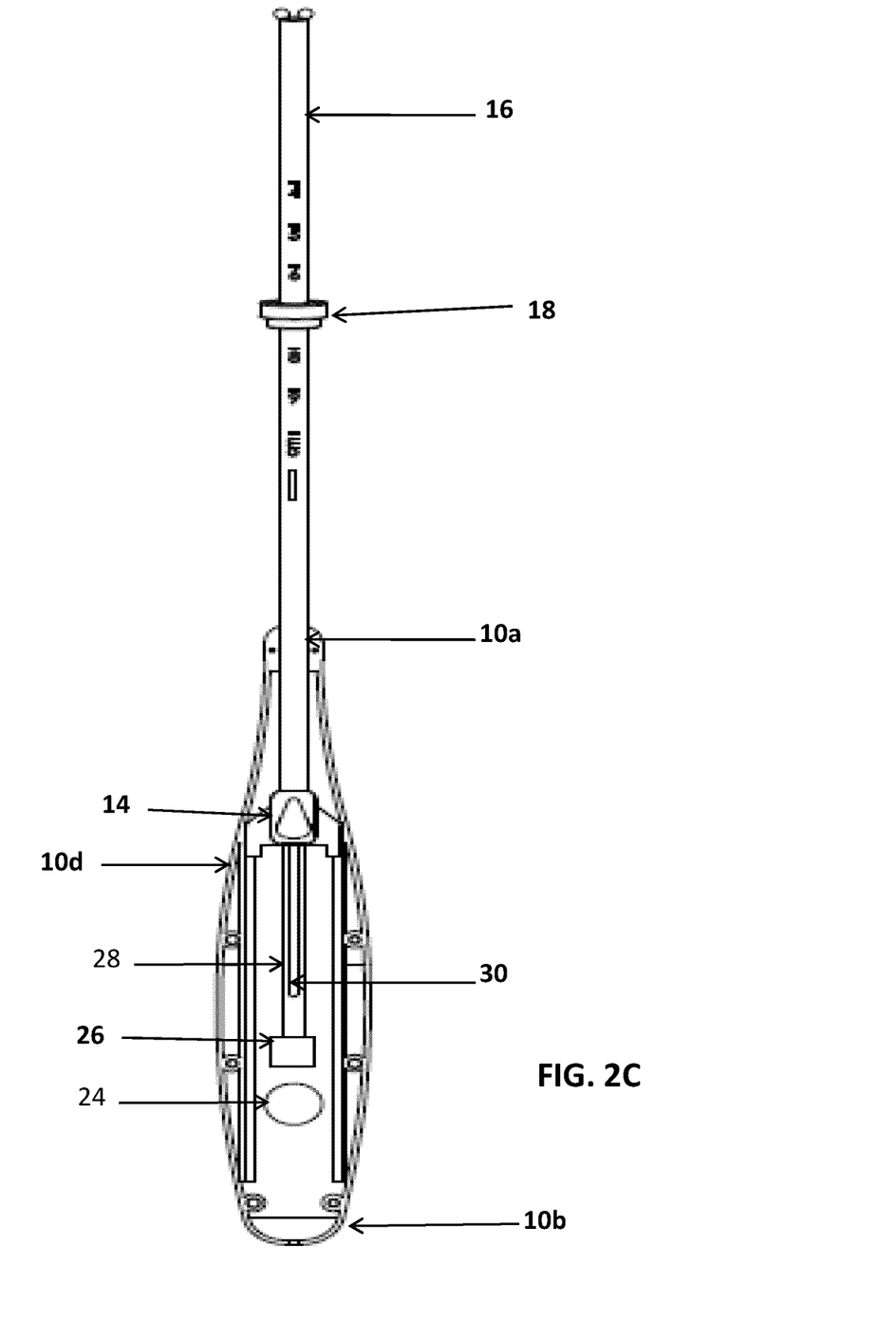

FIG. 2C depicts the assembly of FIG. 2B with the insertion tube 16. The insertion tube 16 has a lumen through which the inner tube 28 is passed. The insertion tube 16 is slidably coupled to the inner tube 28. In an embodiment, the length of the inner tube 28 and the insertion tube 16 is same. Further, at the proximal end 16*a* of the insertion tube 16, the switch 14 is fixedly attached. As shown, when the switch 14 is positioned at the distal end 20*a* of the opening 20, the insertion tube 16 is in the extended position and covers the T-frame 32 entirely.

Figure 2D:
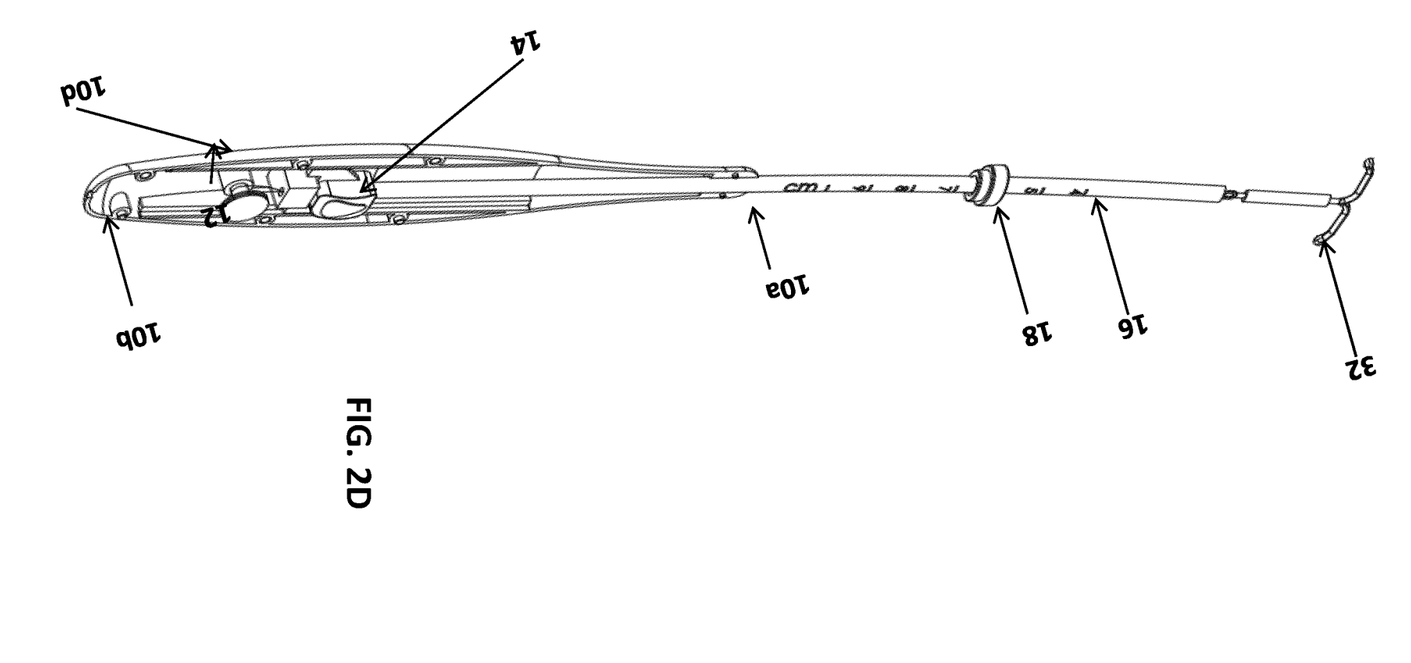

FIG. 2D depicts the assembly of FIG. 2C with the insertion tube 16 completely retracted. In this position, the switch 14 is positioned at the proximal end 20*b* of the opening 20. Due to this, the insertion tube 16 completely covers the inner tube 28 enabling the T-frame 32 to expand completely.

It may be seen from FIGS. 2C and 2D that while there is relative movement between the two tubes 16 and 28, the movement does not dislocate the string 34 connected to the T-frame 32 rather the string 34 is held in place. Further, the string does not tangle with any part/component of the device due to the tension in the string.

Figure 2E:
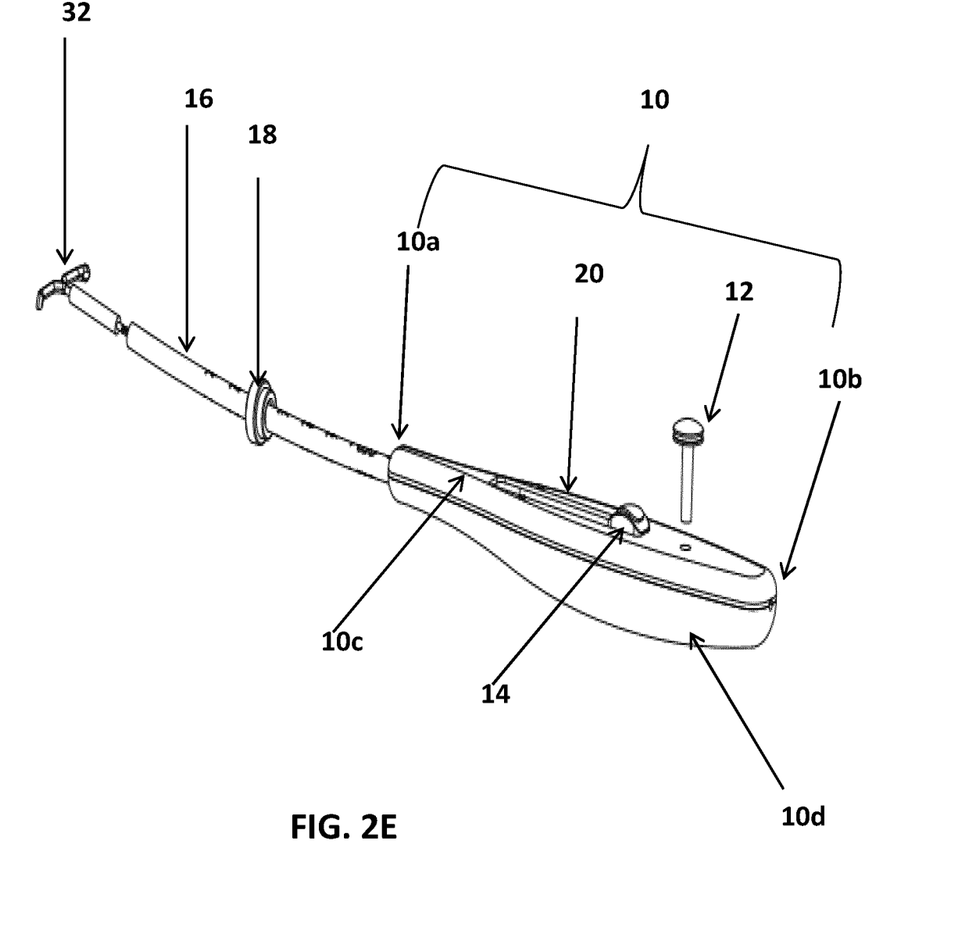

FIG. 2E illustrates the final step of the assembly of the device handle 10. The bottom cover 10*d* of the inserter's handle 10 of FIG. 2C/2D is closed by the upper cover 10*c*. The protrusions/holes of the upper cover 10*c* mate with the corresponding counterparts of the bottom cover 10*d* and hold the internal assembly in place. Thereafter, the safety knob 12 is inserted in the corresponding hole on the upper cover 10*c*, the stem of which mates with the knob hole 24 of the bottom cover 10*d*. The inserter 100 is completely assembled.

Figure 3:
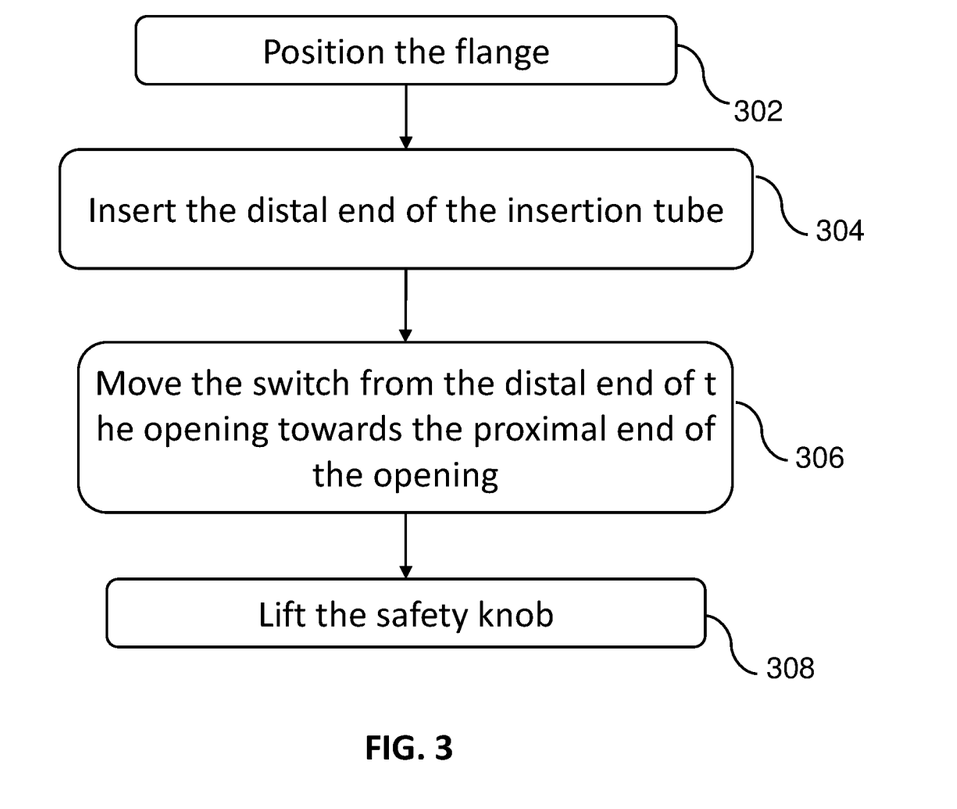
FIG. 3 depicts a flowchart showing steps of operation of the device.

FIG. 3 depicts a flowchart showing steps of operation of the device. At 302, the flange is positioned at the desired marking provided on the insertion tube. The depth of the human anatomy is determined and accordingly, the position of flange is decided. At step 304, the distal end of the insertion tube is inserted inside the human anatomy till the flange touches the human anatomy. The insertion tube cannot be pushed further thereafter. Before the tube is inserted, the switch is positioned at the distal end of the opening due to which the insertion tube completely surrounds the T-frame and is easy to insert inside the human anatomy.

At step 306, the switch is moved from the distal end of the opening towards the proximal end of the opening. As explained in the figures above, this is achieved due to the sliding movement of the switch. However, other means of moving the switch are within the teachings of the present disclosure. Due to the sliding movement, the T-frame expands inside the human anatomy at the inserted location.

At step 308, the safety knob is lifted which leads to the tied end of the string being released. As the inserter is withdrawn from the human anatomy, the string along with the T-frame remains positioned inside the desired location. In case the length of the string exceeds the required length, the extra length can be cut.

From the above, it may be seen that the entire assembly as well as operation of the inserter is highly simplified and does not require highly technical components. Due to this simplified assembly, it is very easy for a surgeon to use the inserter for the intended purpose.

Various modification or additions to the above disclosure are feasible and fall within the teachings of the present disclosure. For example, an illumination source may be coupled to the distal end of the insertion tube. Alternately, the inner tube may not contain a slot.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. An inserter comprising:
 a handle having an upper cover and a bottom cover, the upper cover having a longitudinal opening, said longitudinal opening having a longitudinal axis parallel to a longitudinal axis of the inserter, a proximal end and a distal end, the bottom cover comprising:
  a knob hole in the bottom cover provided to mate with a safety knob removably insertable through the longitudinal opening in the upper cover to mate with the knob hole in the bottom cover,
  a mounting member extending from an inner surface of the bottom cover of the handle, the mounting member having a through-hole; and
  an inner tube having a proximal end and a distal end, the proximal end of the inner tube attached to the mounting member;
 an insertion tube movably coupled to the inner tube with a longitudinal axis essentially parallel to a longitudinal axis of the inner tube, the insertion tube having a proximal end and a distal end;
 a switch coupled to the proximal end of the insertion tube and arranged in the longitudinal opening; and
 a string having a length, a proximal end and a distal end, the proximal end of the string removably coupled to the safety knob, the proximal end of the string being passed through the proximal end of the inner tube and the through-hole of the mounting member, the string being finally wound around the knob hole such that removal of the safety knob from the knob hole releases the string, and the distal end of the string coupled to a device to be inserted inside a human anatomy,
 wherein the length of the string corresponds to the summation of length of the inner tube, width of the mounting member and distance between the mounting member and the knob hole to ensure that the device is held in position.

2. The inserter as claimed in claim 1, wherein the inner tube comprises a lumen through which the string is passed.

3. The inserter as claimed in claim 1, wherein the inserter comprises a flange mounted on the insertion tube to provide an indication of the depth of a human anatomy in which the insertion tube is to be inserted.

4. A kit comprising an intrauterine device and an inserter as claimed in claim 1.

5. A method of operating an inserter, the method comprising:
 mating a safety knob with a knob hole in a bottom cover through an opening in an upper cover, the safety knob being configured to hold a proximal end of a string, wherein the proximal end of the string being passed through an inner tube, a mounting member and finally wound around the knob hole;
 moving a switch to a distal end of an opening;
 introducing an insertion tube in a human anatomy up to a predefined depth, the insertion tube being slidably coupled to the inner tube;
 moving the switch from the distal end to a proximal end of the opening exposing a device inside the human anatomy, the device being provided at a distal end of the inner tube via the string;
 removing the safety knob from the knob hole releasing the string, wherein the string including a length that corresponds to the summation of length of the inner tube, width of the mounting member and distance between the mounting member and the knob hole to ensure that the device is held in position; and
 withdrawing the insertion tube from the human anatomy leaving the device inside the human anatomy.

* * * * *